United States Patent [19]

Bowyer et al.

[11] 4,038,385

[45] July 26, 1977

[54] PROTECTION OF HORTICULTURAL GROWTH

[75] Inventors: Alta M. Bowyer, Los Angeles; George B. Hinckley, Montebello; James E. Davis, Santa Paula, all of Calif.

[73] Assignee: Leffingwell Chemical Company, Brea, Calif.

[21] Appl. No.: 354,685

[22] Filed: Apr. 26, 1973

Related U.S. Application Data

[63] Continuation-in-part of Ser. No. 174,228, Aug. 23, 1971, abandoned, which is a continuation of Ser. No. 717,972, April 1, 1968, abandoned.

[51] Int. Cl.$^2$ ........................................... A01N 11/00
[52] U.S. Cl. ................................. 424/166; 424/196; 424/312; 424/325
[58] Field of Search ................. 424/166, 196, 318, 30, 424/19, 38

[56] References Cited

U.S. PATENT DOCUMENTS

| | | | |
|---|---|---|---|
| 2,019,275 | 10/1935 | Sharples | 424/325 |
| 2,510,367 | 6/1950 | Baumgartner | 424/30 |
| 2,832,714 | 4/1958 | Jolly | 424/30 |

FOREIGN PATENT DOCUMENTS

| | | | |
|---|---|---|---|
| 669,823 | 4/1952 | United Kingdom | 424/325 |
| 994,125 | 6/1966 | United Kingdom | 424/325 |
| 744,993 | 2/1956 | United Kingdom | 424/30 |

OTHER PUBLICATIONS

*Soap and Sanitary Chemicals*, No. 12, Dec. 1949, pp. 40–43 & 147, vol. 25.

Hayne, et al., (Reprint from *The Quarterly Bulletin*), of the Mich. Agri. Exp. Sta., Mich. State Univ., vol. 41, No. 1, pp. 88–98, (8/58).

*Chemical Abstracts*, vol. 56, (1961), p. 10636h.

*Soap and Sanitary Chemicals*, 9/49, pp. 123–125, 127 & 149.

*Chemical Abstracts*, vol. 53, 13500a.

*Primary Examiner*—Frederick E. Waddell
*Attorney, Agent, or Firm*—Louis J. Bachand

[57] ABSTRACT

Protection of horticultural property such as fruit, vegetable and ornamental plants, trees and shrubs against warm-blooded animal predators such as deer and rabbits is achieved by coating the normally edible portions of horticultural growth with a tall oil composition, essentially free of biotically active material and suitably containing a volatile amine which may be prereacted with fatty acids added to or present in the tall oil.

4 Claims, No Drawings

PROTECTION OF HORTICULTURAL GROWTH

REFERENCE TO RELATED APPLICATIONS

This application is a continuation in part of our earlier filed application Ser. No. 174,228 filed Aug. 23, 1971, and now abandoned; said earlier application being in turn a continuation of application Ser. No. 717,972 filed Apr. 1, 1968, also now abandoned. The subject matter of said applications has been carried forward in the presently pending application and the disclosures thereof are hereby incorporated by reference.

BACKGROUND OF THE INVENTION

1. Field of the Invention

This invention has to do with protection of grasses, plants, trees and shrubs, herein referred to as "horticultural growth", from use as feeding stations by foraging animals. Herbivorous animals such as deer typically eat foliage from trees, particularly fruit and nut trees. Rabbits eat the bark of trees and the foliage of low growing vegetables such as carrot tops. Crop yields are much reduced and trees in some instances are lost.

2. Prior Art.

Although mechanical devices such as fences have been the resort in the past, modern protective techniques are chemical. A number of chemicals have been produced for use as animal repellants. These materials appear to operate by making the normally edible portions of horticultural growth bitter or otherwise unpleasant tasting or in some instances toxic to animal species. Chemicals disclosed to be useful for repellency include: thiocyanic acids salts of methylidene amines e.g. diethylenetriamine thiocyanate (U.S. Pat. No. 2,547,722); pentachlorobenzylmercaptan derivative e.g. pentachlorobenzylisothiuronium chloride (U.S. Pat. No. 3,139,379); and 2-naphthenyl imidazoles such as 2-naphthenyl imidazoline. These compounds are unusual, hence relatively expensive and thus not suited to large scale use.

There is a need accordingly for a repellant composition which is highly effective, relatively cheap and preferably already generally recognized as safe for use on agricultural products.

SUMMARY OF THE INVENTION

It is a major objective of the invention to provide for the protection of horticultural growth against herbivorous pests by a means which is inexpensive, easily implemented and safe.

It has now been discovered that horticultural growth may be protected against consumption by warm-blooded predators by application of a tall oil composition to portions of growth accessible to such predators. The tall oil composition is used as a repellant only and accordingly is essentially free of additives or components having an appreciable or intended effect on plant growth rates or insect conditions i.e. biotically active ingredients which are normally used or useful for growth or insect regulation.

Application of the tall oil is to the surface by any convenient means such as brushing, spraying or flushing. Accordingly carriers facilitating application such as low viscosity inert liquids, especially water are useful for carrying the tall oil to the growth to be treated e.g. as a dispersion or intimate mixture.

Volatile amines(which term includes ammonia herein) both primary and secondary and having up to 10 carbon atoms can be added to the tall oil composition for the specific purpose of contributing additional repellancy. Longer term effects are realized if the amine is tied up in the composition e.g. by reaction with a fatty acid such as occurs naturally in the tall oil i.e. oleic acid or an added acid e.g. stearic acid. Such reaction provides an amine soap which contributes to leaf wetting by the tall oil. Preferably the amine additive if any is ammonia and is present in an amount providing a highly alkaline pH to the applied composition e.g. between pH 8 and 12.

Application of the present composition as described provides horticultural growth repellant to warm-blooded predators which comprises normally animal-edible portions of the growth and a coating thereon of a composition consisting essentially of tall oil free of biotically active ingredients. Preferred characteristics of the tall oil used include a weight ratio of unsaponifiable material to rosin acids above 0.7, a maximum of 35 weight per cent rosin acids and particularly a minimum of 25 weight per cent unsaponifiable material and an acid number not less than 100.

DESCRIPTION OF THE PREFERRED EMBODIMENTS

Tall oil is a naturally occurring product which is separated from pine wood during pulping operations. While there are variations in the composition of the tall oils available commercially, because of geographic origin or recovery techniques, typical analyses range from 40 to 50 per cent rosin acids and a like amount of fatty acids with about 10 per cent neutral or "unsaponifiable" material. The rosin acids will include abietic, levopimaric, neoabietic, dehydroxyabietic, dextropimaric and isodextropimaric acids, all having the empirical formula $C_{19}H_{29}COOH$. The fatty acids are essentially oleic and linoleic acids with small amounts of linolenic and palmitic acids. The neutral fraction is typically composed of esters of fatty acids, about 60 per cent, and the balance sterols (esp. $\beta$-sitosterol), higher alcohols and hydrocarbons, generally terpenes.

The naturally occurring tall oils may be concentrated by distillation to increase the concentration of the higher boiling components. In certain repellant compositions, herein, the tall oil is so modified, to comprise basically the pitch and light ends of the natural product, to have desirably a maximum of 10 to 35 weight per cent rosin acids and a minimum of 25 and preferably 35 weight per cent unsaponifiable material (terpenes etc.), and particularly a weight ratio of unsaponifiable material to rosin acids of above 0.7 and particularly greater than 2.5. Accordingly fatty acid content may range above about 50 per cent and desirably be between 52 and 70 per cent, by weight. A further characteristic of preferred tall oil is an acid number (in milligrams KOH per gram of tall oil) of not less than 100 and desirably between 110 and 190.

As stated, the tall oil compositions used herein are free of biotically active ingredients including plant hormones, and fertilizers and insecticides, herbicides, fungicides, miticides and like biocidal materials.

The tall oil is applied to the horticultural growth by brushing or spraying or dusting in admixture with a suitable carrier e.g. and preferably water for low cost, or as an inert powder. Amounts of 2 to 50 weight per cent tall oil in an aqueous carrier are satisfactory for storage and shipment, to be further diluted to desirable viscosity for application.

Wet coverage is best and to insure good spreading a surfactant may be employed. Among suitable surfactants are anionic aromatic compounds such as the water soluble higher alkyl aryl sulfonates, particularly benzene sulfonates having 8 to 15 carbon atoms in the alkyl group; and normal and secondary higher alkyl sulfates especially lauryl sulfate and other polyalcohol esters of sulfuric acid esterified with a fatty acid. The sulfates and sulfonates are used as the water-soluble salts, such as the alkali metal and nitrogen containing e.g. lower alkylolamine salts. Other, nonionic, surfactants are useful for leaf wetting e.g. the alkylene oxide derivatives of hydrophobic organic groups such as alkyl phenols, esters and alcohols e.g. sorbitol and sorbitan fatty esters, organic acids and amides including fatty and rosin acids and amides as well as synthetic acids and amides.

Certain of these surfactants may be formed in situ by additon of an amine to the tall oil and reacting with the fatty acid components of the oil. Thus, ammonia added to the tall oil and reacted will form ammonium oleate, an effective surfactant. Similarly alkanolamines of 2 to 6 carbon atoms especially ethanolamines and isopropanolamine as well as primary e.g. ethyl, propyl, butyl and secondary diethyl, dipropyl and dibutyl amines may be reacted with fatty acids to promote leaf surface wetting by the tall oil e.g. by reducing the surface tension of the applied composition to less than 45 dynes/centimeter, at 25° C.

It has been observed that the amine component if volatile per se or on release from a tied-up form such as an oleate contributes to repelling of animal species, owing no doubt to olefactory and organoleptic unattractiveness characteristic of the amines.

While the fatty acid present in tall oil provides a convenient source of acid for combination with amine, other and/or additional acids may be incorporated in the tall oil composition. The quantity of amine added is variable from an amount providing perceptible short term improvement in repellency to that capable of combining significantly with fatty acids present and neutralizing the acids or added for leaf wetting and slow release purposes and beyond that to amounts in excess of those neutralizing fatty acids present and capable of altering the tall oil pH e.g. to between 8 and 12 which has been found to be a highly desirable range for compositions to be sprayed as an intimate aqueous mixture onto foliar surfaces. Thus amounts of amine between 2 and 10 weight per cent of an aqueous carrier formulation containing 3 to 10 weight per cent tall oil and amounts of added fatty acids between 2 and 10 weight per cent are highly satisfactory. Such a formulation would contain from 70 to 93 weight per cent water.

Typical combinations of tall oil properties useful in the present invention are as follows:

TABLE

| Tall Oil | Acid No. | Fatty Acids | Rosin Acids | Unsaponifiables |
|---|---|---|---|---|
| A | 164 | — | 33–35 | 10.4 |
| B | 172 | 49 | 37 | 9 |
| C | 185 | 48 | 45 | 2.9 |
| D | 30–55 | 4–10 | 12–30 | 30–40 |
| E | 110–120 | 52–58 | 1–3 | 35–40 |
| F | 175 | 85 | 2.3 | 11 |
| G | 173–183 | — | 8–10 | 6–10 |
| H | 184 | 54 | 37.5 | 4.3 |
| I | 145 | 41 | 30 | 29 |

A tall oil composition was prepared by blending tall oil E of the Table (3.5) with aqua ammonia (5.5), oleic acid (7.5), stearic acid (2.5) and water (81) all in weight per cent.

EXAMPLE 1

The above-formulation was diluted with water at the rate of 5 gallons to 100 gallons of water and sprayed on newly planted walnut trees in an area where deer had been feeding. No deer feeding damage occurred during spring and summer.

EXAMPLE 2

Example 1 was duplicated using 3 and 4 year old lemon trees previously subjected to extensive damage through deer feeding. Application in September forestalled further feeding until winter rains. Deer were not observed in the orchard area after spraying.

EXAMPLE 3

Example 1 was duplicated on various citrus groves but at an application level of 2.5 gallons of the tall oil composition per 100 gallons of spray. Again repelling was totally effective while the foliage was coated.

EXAMPLE 4

Flowers being grown commercially and including snap dragons and petunias were sprayed with the formulation of Example 3 at the rate of 50 gallons per acre through row crop sprayers, drip hoses and T-jet nozzles. Prior to spraying deer had begun feeding on plants reaching the 3 or 4 leaf stage. After application feeding was stopped.

EXAMPLE 5

A home yard containing various ornamentals was sprayed using a small hand held sprayer with the formulation of Example 3. Deer feeding on rose bushes and other plants was immediately arrested.

EXAMPLE 6

A formulation containing one-half gallon of the tall oil composition per 100 gallons of water was sprayed over egg plants which were being attacked by cottontail rabbits. After application no more plants were disturbed. It is noteworthy that only the outside rows of plants were treated but that rabbits did not pass through the treated rows to the untreated plants.

EXAMPLE 7

A home garden containing growing lettuce, carrots and beets was treated by spraying with the formulation of Example 1. Rabbit feeding on all plants ceased after application.

EXAMPLE 8

Flower seedlings in flats were sprayed by hand with the formulation of Example 1. Thereafter nibbling of the seedlings by browsing rabbits was stopped with no further losses.

EXAMPLE 9

Prune trees were being badly girdled by rabbits. The tall oil composition at a concentration of 2 gallons per 100 of water was coated onto the trunks of the trees. No further damage occurred.

EXAMPLE 10

Purslane growing between rows of rubber trees was treated at two levels of concentration, one half gallon of tall oil composition and 2 gallons per 100 gallons of water. Rabbit feeding on the purslane was arrested by both formulations. Overhead watering several times a week eventually washed away the repellant. The higher concentration was effective 5 weeks; the lower 3 weeks.

EXAMPLE 11

Star jasmine (trachelospermum jasminoides) in gallon cans were eaten by rabbits to unsaleability. The tall oil composition at 2 gallons per 100 of water prevented further eating and within 3 weeks new growth permitted sale of the plants.

EXAMPLE 12

The repellant composition disclosed herein is highly effective and nontoxic. To demonstrate this under controlled conditions, several tame deer were penned and fed green alfalfa, dry alfalfa and carrots which had been variously treated by hand spraying with the tall oil composition at concentrations of 0 and ¼ to 3 gallons per 100 gallons of water. The length of time until the deer started feeding on the specimens was observed. After one day all untreated food was gone. Carrots having less than 2 gallons concentrated spray were eaten after one day. But similarly treated alfalfa was not eaten until after the second day. The food treated at 2 and 3 gallons was not eaten until the fourth day.

EXAMPLE 13

Example 1 is duplicated employing unmodified tall oil dispersed in water. Results are good, particularly where good coverage was secured by spray application.

EXAMPLE 14

A tall oil composition was prepared by blending aqua ammonia, water (preheated to 150°-160° F) and tall oil I of the Table as follows:

| Tall Oil I | 45 weight % |
| Water | 45 weight % |
| Aqua Ammonia (26° Be) | 10 weight % |

This relatively viscous mixture was diluted 1 to 50 with water for spray application. Results are equivalent to those of previous examples.

EXAMPLE 15

A tall oil composition was prepared by blending aqua ammonia, water (preheated to 150°-160° F) and tall oil I of the Table as follows:

| Tall Oil I | 15 weight % |
| Water | 82 weight % |
| Aqua Ammonia | 3 weight % |

This thin solution is diluted 1 to 5 with water for application. Results are generally equivalent in repellency although much of the thin fluid appeared to run off the foliage of the plants.

EXAMPLES 16-19

Tall oil compositions were prepared from the indicated materials by first mixing the tall oil and acids in water and melting at 150°-160° F. Ammonia is then added and mixed for 5-10 minutes. All proportions are by weight. Letter identification of tall oils is from the Table.

| 16. | Tall Oil D | 4.5% |
| | Stearic Acid | 3.0% |
| | Oleic Acid | 7.5% |
| | Water | 80.0% |
| | Ammonia 26° Be | 5.0% |
| 17. | Tall Oil A | 5.0% |
| | Stearic Acid | 3.0% |
| | Oleic Acid | 7.0% |
| | Water | 79.0% |
| | Ammonia 26° Be | 6.0% |
| 18. | Tall Oil I | 3.5% |
| | Stearic Acid | 3.5% |
| | Oleic Acid | 11.0% |
| | Water | 75.0% |
| | Ammonia | 7.0% |
| 19. | Tall Oil E | 2.0% |
| | Tall Oil D | 2.0% |
| | Oleic Acid | 8.0% |
| | Stearic Acid | 3.0% |
| | Polyoxyethylene sorbitol oleate | 1.0% |
| | Water | 78.0% |
| | Ammonia | 6.0% |

The foregoing formulations are evaluated and found to be effective repellants. Variations in formulations are primarily useful to obtain desirable fluid characteristics.

EXAMPLES 20A and 20B

Example 16 is duplicated using ethyl amine (20A) and ethanolamine (20B) in place of ammonia. Results are equivalent.

I claim:

1. A method of repelling deers and rabbit predators from horticultural growth which consists in releasing from a coating on said growth a predator repelling volatile agent selected from the group consisting of primary or secondary amines having up to 10 carbon atoms and ammonia, said agent being released from a coating on said growth to be protected, said coating having been applied as an aqueous composition consisting essentially of 70 to 93 percent water, 3 to 10 percent tall oil and 2 to 10 percent of said agent sufficient to provide a pH between 8 and 12 in said composition as applied.

2. The method of claim 1 in which oleic or stearic acid is present in said composition in an amount between 2 and 10 percent by weight in the composition applied to said growth.

3. The method of claim 1 in which said agent is ammonia.

4. The method of claim 1 in which said agent is an amine selected from the group consisting of ethyl, propyl, butyl, diethyl, dipropyl and dibutyl amines and alkanolamines having 2 to 6 carbon atoms.

* * * * *